United States Patent [19]

Kaneko et al.

[11] 4,427,588

[45] Jan. 24, 1984

[54] PROCESS FOR CONVERSION OF OXOTOMAYMYCIN TO TOMAYMYCIN

[75] Inventors: Takushi Kaneko; Henry S. L. Wong, both of Fayetteville, N.Y.

[73] Assignee: Bristol-Myers Company, New York, N.Y.

[21] Appl. No.: 439,965

[22] Filed: Nov. 8, 1982

[51] Int. Cl.³ .......................................... C07D 487/04
[52] U.S. Cl. .............................................. 260/239.3 T
[58] Field of Search ................................. 260/239.3 T

[56] References Cited

PUBLICATIONS

Arima et al., "J. Antibiotics", vol. 25, No. 8, pp. 437–444, (1972).
Kariyone et al., "Chem. Pharm. Bull.", vol. 19, No. 11, pp. 2289–2293, (1971).
Leimgruber et al., "J. Am. Chem. Soc.", vol. 90, pp. 5641–5643, (1968).
Derwent Abstract of Japanese Patent J5 4073-195, Jun. 12, 1974, Japanese Patent Publication 73195/75.

*Primary Examiner*—Robert T. Bond
*Attorney, Agent, or Firm*—David M. Morse

[57] ABSTRACT

A new chemical procedure for conversion of the biologically inactive fermentation product, oxotomaymycin, to the antibiotic, tomaymycin is disclosed as well as novel intermediates employed in such procedure.

18 Claims, No Drawings

PROCESS FOR CONVERSION OF OXOTOMAYMYCIN TO TOMAYMYCIN

BACKGROUND OF THE INVENTION (1) Field of the Invention

This invention relates to a novel process for conversion of the biologically inactive fermentation product, oxotomaymycin, to the antibiotic, tomaymycin, which has been demonstrated to have antitumor, antiviral and antibiotic activities.

(2) Description of the Prior Art

The antibiotic tomaymycin, having the formula

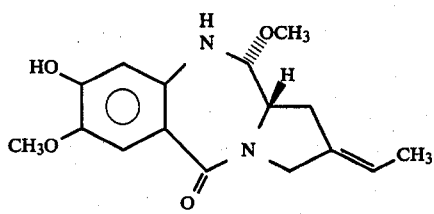

I is disclosed in *J. Antibiotics* 25: 437–444 (1972) as being isolated from the fermentation broth of *Streptomyces achromogenes* var. *tomaymyceticus*. More recently, isolation of tomaymycin from a Nocardia species culture has been reported in Japanese Patent Publication No. 73195/79. Tomaymycin may be isolated either as a crystalline methanol adduct (formula I) or as desmethanol tomaymycin of the formula

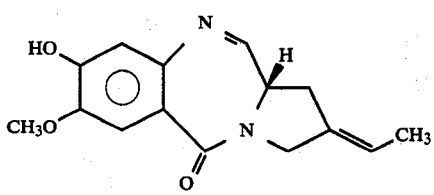

Ia depending on the solvent used in the final step of its isolation. Both forms of the antibiotic appear to have antimicrobial, antiviral and antitumor activities.

While tomaymycin displays useful biological activities, another product of the same fermentation broth named oxotomaymycin has been disclosed in *Chem. Pharm. Bull.* 19: 2289–2293 (1971) as being biologically inactive. Oxotomaymycin has the structural formula

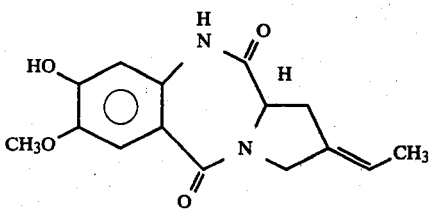

II

If available, a method to convert the biologically inactive fermentation product, oxotomaymycin, to tomaymycin (or desmethanol tomaymycin which can be easily obtained from tomaymycin by heating in a non-methanol solvent) would be of considerable utility. This is particularly true since tomaymycin and desmethanol tomaymycin are chemically unstable and their isolation from a fermentation broth is quite challenging, whereas, being much more stable, oxotomaymycin can be isolated in a straightforward manner. Thus, the preparation of tomaymycin could be greatly facilitated by first isolating oxotomaymycin and then converting this purified material to tomaymycin by a chemical procedure.

*J. Am. Chem. Soc.* 90: 5641–5643 discloses a total synthesis of anthramycin of the formula

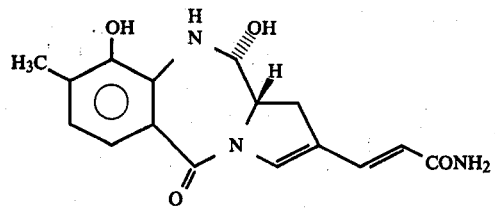

by a process involving the intermediate of the formula

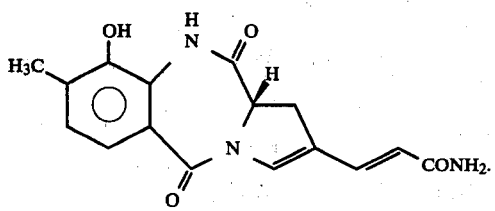

Attempts to reduce the tertiary amide group of this intermediate were unsuccessful, and it was necessary to prepare a benzoxazoline intermediate of the formula

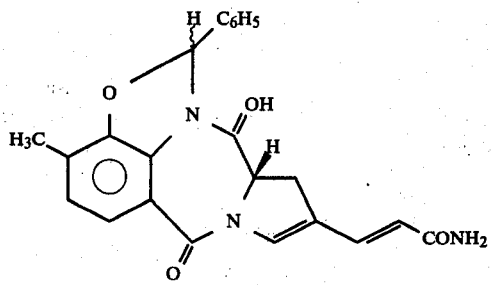

and then reduce this amide derivative to the desired carbinolamine product.

SUMMARY OF THE INVENTION

The present invention provides a method for converting the biologically inactive fermentation product, oxotomaymycin, to the antibiotic, tomaymycin. By this method the preparation of tomaymycin can be greatly facilitated.

As mentioned above tomaymycin has been isolated in a methanol adduct form (named herein as tomaymycin) and as a desmethanol form (named herein as desmethanol tomaymycin). The two forms of the antibiotic are interconvertible. Thus, for example, tomaymycin may be converted to desmethanol tomaymycin by refluxing in chloroform (*J. Antibiotics* 25: 437–444, 1972) or heating under reduced pressure (*Chem. Pharm. Bull.* 19: 2289–2293, 1971). Also, the methanol adduct form may be subjected to a silica gel thin layer chromatography procedure using 5% methanol-methylene chloride as the solvent to convert it to the desmethanol form. The desmethanol form may be easily converted to tomaymycin or another alcohol adduct form by recrystallization from the appropriate alcohol (*J. Antibiotics*

The process of the present invention comprises the steps of (1) converting oxotomaymycin of the formula

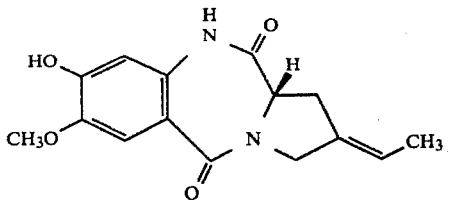

to the corresponding 8-OH protected intermediate of the formula

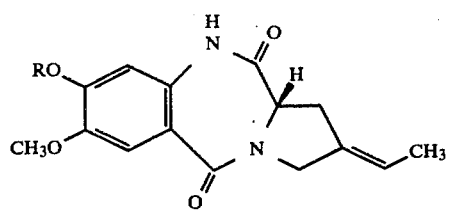

wherein R is a conventional phenolic hydroxyl protecting group;

(2) reacting amide derivative III with phosphorous pentasulfide or 2,4-bis(4-methoxyphenyl)-1,3-dithia-2,4-diphosphetane-2,4-disulfide in an inert organic solvent to produce the thioamide intermediate of the formula

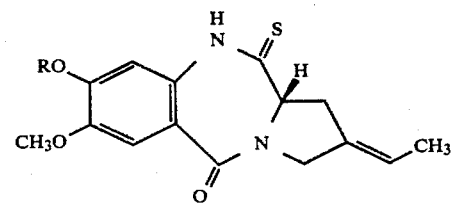

wherein R is as defined above;

(3) reacting intermediate IV with a (lower)alkyl halide or (lower)alkoxonium salt in an inert organic solvent and in the presence of base to produce the thioiminoether intermediate of the formula

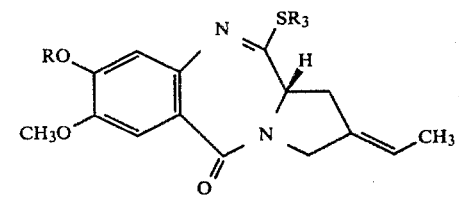

wherein $R_3$ is (lower)alkyl and R is as defined above;

(4) optionally removing the C-8 hydroxyl protecting group of intermediate V to form an intermediate of the formula

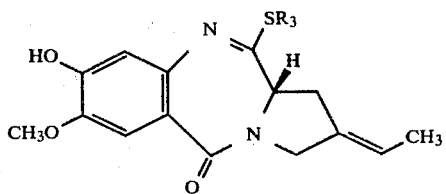

wherein $R_3$ is as defined above;

(5) selectively reducing the thioiminoether moiety of intermediate V or VI in an inert solvent to produce a thiocarbinolamine intermediate of the formula

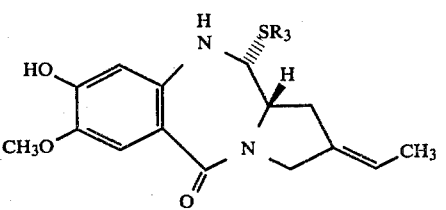

or

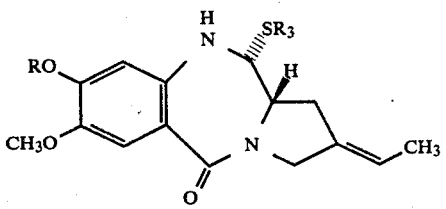

wherein R and $R_3$ are as defined above; and (6) reacting intermediate VII or VIII with a mercuric salt in methanol to form the carbinolamine product of the formula

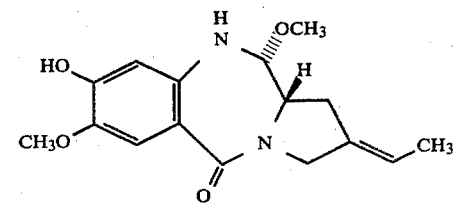

or

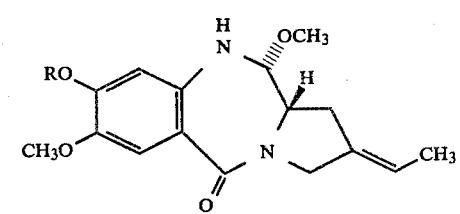

wherein R is as defined above; and, when the product obtained is compound IX, removing the hydroxyl protecting group R from intermediate IX so as to form the desired tomaymycin product I; and, if desired, converting tomaymycin to desmethanol tomaymycin of the formula

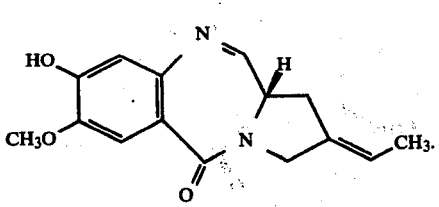

Ia

In another aspect the present invention provides the novel intermediates of formulae IV, V, VI, VII and VIII and procedures for their synthesis. Preferred process embodiments comprise reaction step (2) of the above-described process for preparation of intermediate IV, step (3) for preparation of intermediate V, step (4) for preparation of intermediate VI, and step (5) for preparation of intermediates VII and VIII.

DETAILED DESCRIPTION

To elaborate on the above-described process, step (1) involves protection of the C-8 hydroxyl group of oxotomaymycin with a conventional phenolic hydroxyl protecting groups such as acetyl, trifluoroacetyl, benzoyl, p-nitrobenzoyl, p-methoxybenzoyl or vinyloxycarbonyl which can be removed by mild base or trimethylsilyl, t-butyldimethylsilyl or diphenylmethylsilyl which can be removed with fluoride ion. Conveniently, the C-8 hydroxyl group is selectively acylated by a conventional acylating reagent such as 1~1.5 equivalent of acid chloride (e.g. benzoyl chloride) or acid anhydride (e.g. acetic anhydride) and 1~1.5 equivalent of base. For the base, pyridine, triethylamine and sodium hydride may be used. The preferred reagent system is benzoyl chloride (1.1 equivalent) as an acylating agent, NaH (1.1 equivalent) as the base, and dimethyl formamide as the solvent. Another preferred protecting group for the C-8 hydroxy group is a (lower)organosilyl ether (the term "lower" used herein and in the claims refers to $C_1-C_6$ carbons). For silylation the preferred base is imidazole or triethylamine and the preferred solvent is dimethyl formamide. Both acylation and silylation can be carried out at ~0° C. to room temperature. The phenolic hydroxyl protecting group is selected so as to withstand the reaction conditions of steps (2) through (3) of the process and to be removable without any significant disruption of the pyrrolo[1,4]benzodiazepine ring system. Examples of suitable phenolic hydroxyl protecting groups and methods for their introduction and removal are described in the literature e.g. *Protective Groups in Organic Chemistry*, T. W. Greene, Ed., Wiley-Interscience, New York, 1981, Chapter 3.

Step (2) involves thiation of amide intermediate III to form thioamide intermediate IV. Thiation is carried out by reacting III in an inert organic solvent such as benzene, toluene, dioxane, and the like, with phosphorous pentasulfide or 2,4-bis(4-methoxyphenyl)-1,3-dithia-2,4-diphosphetane-2,4-disulfide (Lawesson's reagent). The molar ratio of the thiation reagent to amide III should be about 0.5~1.0 and preferably 0.5. The reaction temperature may be between about 50° C. to 150° C. The most preferred thiation reagent is Lawesson's reagent.

In step (3) the thioamide intermediate IV is alkylated to form thioiminoether intermediate V with a (lower)alkyl halide or (lower)alkoxonium salt in an inert organic solvent (e.g. tetrahydrofuran, methylene chloride, etc.). The preferred reagent-solvent system is methyl iodide (1~5 equivalents) in tetrahydofuran or triethyloxonium tetrafluoroborate (1~1.5 equivalents) in methylene chloride. The alkylation reaction is typically carried out at about 0° C. to room temperature in the presence of an inorganic base (5–10 equivalents) such as $K_2CO_3$ or $NaHCO_3$.

After formation of intermediate V, the C-8 hydroxyl protecting group may be cleaved by standard procedures. For example, if the protecting group is acyl, it may be cleaved with mild base such as methanolic $K_2CO_3$ or dilute aqueous NaOH solution. Similarly, if the protecting group is organosilyl (e.g. trimethylsilyl), it may be cleaved with a fluoride salt such as tetra-n-butylammmonium fluoride. Since the thioiminoether intermediate is relatively labile, the deprotection reaction should be carried out below room temperature, preferably at about 0° C.

Instead of removing the hydroxyl protecting group at this stage of the overall process, one can proceed directly to reduction step (5) and carry out the deprotection step after either step (5) or step (6). Since, however, step (6) is conveniently carried out without isolating intermediate VII or VIII, i.e. steps (5) and (6) are done in a "one pot" reaction, it is most advantageous to carry out deprotection either prior to reduction step (5) or after formation of carbinolamine I in step (6).

In step (5) the hydroxyl-protected intermediate V or de-protected intermediate VI is selectively reduced in an inert solvent to the corresponding thiocarbinolamine intermediate VIII or VII. This reduction step is preferably carried out by reaction with about one to twenty equivalents of aluminum amalgam in an aqueous ether such as diethyl ether, tetrahydrofuran or dioxane. The reaction can be carried out at from about −5° C. to room temperature, the preferred temperature being about 0° C. The reduction may also be carried out electrochemically using a $PbO_2$ electrode on a two-phase mixture of 10% aqueous $HClO_4$ solution and a halohydrocarbon (e.g. $CH_2Cl_2$, $CHCl_3$, and the like). Electrolytic reduction is done at about 0°–50° C. under a current density of 10–20 mA/$cm^2$ (Japanese Patent Publication No. 29588/82).

After formation of the thiocarbinolamine intermediate VIII or VII, the alkylthio group of the intermediate is replaced with a methoxy group by treatment of the reduction mixture with about 0.5 to 1 equivalent of a mercuric salt (e.g. $HgCl_2$, $HgSO_4$, $Hg(CH_3COO)_2$, $HgBr_2$, etc.) in methanol. The exchange reaction (6) is carried out between about −10° C. and +30° C., preferably at about 0° C.

At the conclusion of step (6), the product is deprotected as in step (4) if hydroxyl protecting group R is still present.

Step (6) of the process normally produces the methanol adduct form of tomaymycin. This form, however, can be converted to desmethanol tomaymycin by an additional step. For example, the methanol adduct form can be subjected to silica gel thin layer chromatography at 5° C. using 5% $CH_3OH$—$CH_2Cl_2$ as the solvent system. Alternatively, the methanol adduct form can be dissolved in chloroform and refluxed for about an hour as described in *J. Antibiotics* 25: 437–444 (1972) or heated under reduced pressure as described in *Chem. Pharm. Bull.* 19: 2289–2293 (1971).

Similarly, if the tomaymycin product is obtained according to the present process in the desmethanol tomaymycin form, this form can be converted to the methanol adduct form by treatment with methanol.

The following examples are not limiting but are intended to be illustrative of the present invention. Melting points were determined on a Thomas-Hoover capillary apparatus and are uncorrected. NMR spectra were obtained on a Varian XL-100 or Bruker WM 360 spectrometer using tetramethylsilane as the internal standard. IR spectra were obtained on a Beckman 4240 spectrophotometer. Mass spectra were recorded on Dupont DP-102 by direct introduction probe. Optical rotation measurements were taken on a Perkin-Elmer 241 MC polarimeter.

EXAMPLE 1

Preparation of Tomaymycin

A. Oxotomaymycin Benzoate

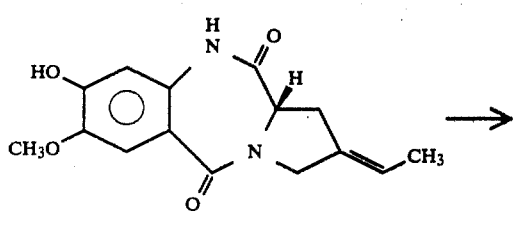

1

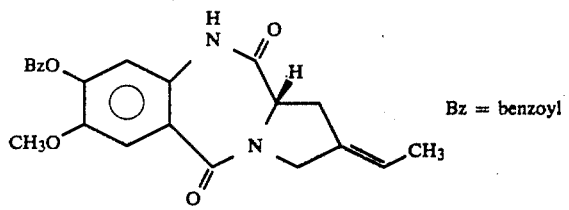

2

Bz = benzoyl

Oxotomaymycin 1 (600 mg, 2.08 mmol) was added at 0° C. to a suspension of NaH (65 mg, 2.70 mmol) in 10 ml of dimethylformamide (DMF). After 1 hour of stirring at room temperature, the solution was cooled to −20° C., and benzoyl chloride (380 mg, 2.70 mmol) was added dropwise. Stirring was continued for 1 hour at −20° C. and the DMF was removed under reduced pressure. Water was added to the residue, and the resulting precipitate was collected by filtration. The solid was re-dissolved in 10% $CH_3OH$—$CH_2Cl_2$, and this solution was dried over $MgSO_4$. The residue obtained after removal of the solvent was precipitated from $CH_2Cl_2$-ether to give 600 mg (74% yield) of the title compound 2: mp 213°-215° C.; IR(KBr) 3250, 1745, 1697, 1640, 1519, 1430, 1265, 1245, 1220 cm$^{-1}$; NMR ($CDCl_3$, δ) 1.74(bd, 3H, J=7 Hz), 2.66(dd, 1H, J=16, 10 Hz), 3.53(d, 1H, J=16 Hz), 3.89(s, 3H), 4.16(d, 1H, J=16 Hz), 4.32(dd, 1H, J=10, 2 Hz), 4.43(d, 1H, J=16 Hz), 5.55(bd, 1H, J=7 Hz), 6.91(s, 1H), 7.41-7.71(m, 4H), 8.08(bs, 1H), 8.22(dd, 2H, J=8, 2 Hz).

B. Thioxotomaymycin Benzoate

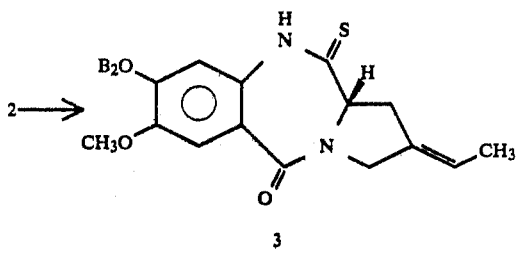

3

A solution of oxotomaymycin benzoate (2, 600 mg, 1.53 mmol) and 2,4-bis(4-methoxyphenyl)-2,4-dithioxo-1,3,2,4-dithiadiphosphate (Lawesson's reagent, 365 mg, 0.903 mmol) in 25 ml of benzene was refluxed for 2 hours. Additional Lawesson's reagent (300 mg, 0.742 mmol) was added and refluxing was continued for 1 hour. The solvent was evaporated and the residue was chromatographed on silica gel to give 290 mg (37%) of the title compound 3: mp 240°-242° C.; IR(KBr) 3440, 1745, 1638, 1609, 1494, 1433, 1245, 1219 cm$^{-1}$; NMR ($CDCl_3$, δ) 1.76(bd, 3H, J=7 Hz), 2.74(dd, 1H, J=16, 10 Hz), 3.92(s, 3H), 3.95(d, 1H, J=16 Hz), 4.15(d, 1H, J=16 Hz), 4.45(d, 1H, J=16 Hz), 4.46(dd, 1H, J=10, 2 Hz), 5.57(m, 1H), 6.98(s, 1H), 7.45-7.70(m, 4H), 8.23(dd, 1H, J=8, 2 Hz), 9.48(bs, 1H).

C. Desmethanol Tomaymycin

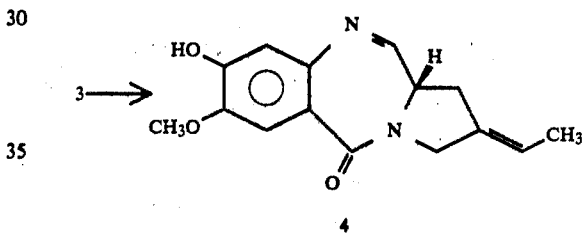

4

Thioamide 3 (250 mg, 0.612 mmol) and methyl iodide (305 mg, 2.15 mmol) in 10 ml of tetrahydrofuran (THF) containing 590 mg $K_2CO_3$ were stirred at room temperature for 18 hours. The reaction mixture was filtered, and the THF was evaporated to give 260 mg of the thioimino ether (NMR: a 3H singlet at 2.40 δ for $SCH_3$).

This material was dissolved in 2 ml of $CH_3OH$ and treated at 0° C. for 1 hour with 6 ml of saturated $K_2CO_3$—$CH_3OH$. The reaction mixture was neutralized with 10% HCl solution and extracted with 10% $CH_3OH$—$CH_2Cl_2$. The organic layer was dried over $MgSO_4$, and then the solvent was removed under reduced pressure to give approximately 200 mg of an oil. This material was dissolved in 10 ml of THF and 1 ml of saturated $KH_2PO_4$ solution. Aluminum amalgam, prepared from 162 mg of aluminum foil, was added and the solution was stirred at 0° C. under a $N_2$ atmosphere for 18 hours. At the end of this period, $Na_2SO_4$ was added and the solution was filtered through CELITE. The filtrate was evaporated and the residue was treated at 0° C. with 3 ml of 0.1 N methanolic $HgCl_2$ solution. The precipitate was filtered off and the solvent was evaporated. The residue was purified by a silica gel TLC at 5° C. (5% $CH_3OH$—$CH_2Cl_2$). Extraction of the major band gave 60 mg of crude desmethanol tomaymycin. This material was dissolved in acetone and precipitated with ether to give 26 mg (16% yield) of the title compound 4: mp 160°-162° C.; IR(KBr) 3365, 1595, 1506, 1436, 1275, 1203 cm$^{-1}$; NMR ($CDCl_3$, δ) 1.74(bd, 3H, J=6 Hz), 2.96(m, 2H), 2.89(m, 1H), 4.00(s, 3H), 4.27(m, 2H), 5.58(m, 1H), 6.90(s, 1H), 7.53(s, 1H), 7.68(d, 1H, J=5 Hz); [α]$_D^{24}$=+191° (C=0.058, pyridine); observed mass 272.1134 (84%), calc'd for $C_{15}H_{16}N_2O_3$: 272.1160.

We claim:

1. A process for the preparation of a compound of the formula

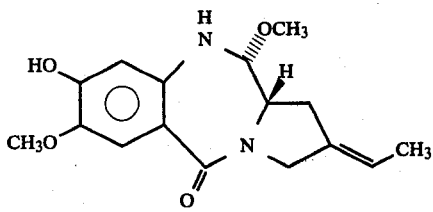

which comprises the steps of (1) converting oxotomaymycin of the formula

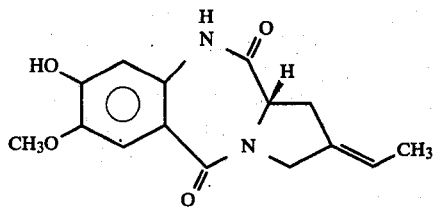

to the corresponding 8-OH protected intermediate of the formula

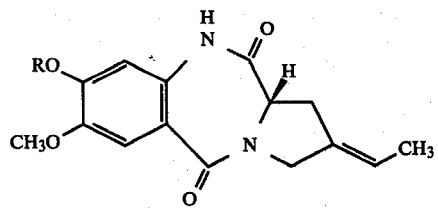

wherein R is a conventional phenolic hydroxyl protecting group;

(2) reacting amide intermediate III with phosphorous pentasulfide or 2,4-bis(4-methoxyphenyl)-1,3-dithia-2,4-diphosphetane-2,4-disulfide in an inert organic solvent to produce the thioamide intermediate of the formula

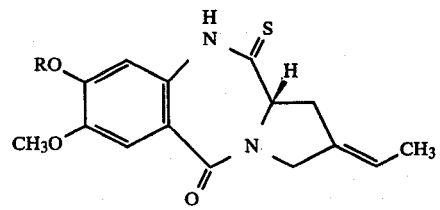

wherein R is as defined above;

(3) reacting intermediate IV with a (lower)alkyl halide or (lower)alkoxonium salt in an inert organic solvent and in the presence of base to produce the thioiminoether intermediate of the formula

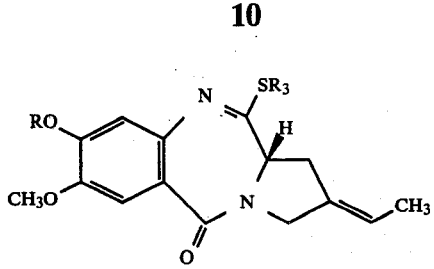

wherein $R_3$ is (lower)alkyl and R is as defined above;

(4) optionally removing the C-8 hydroxyl protecting group of intermediate V to form an intermediate of the formula

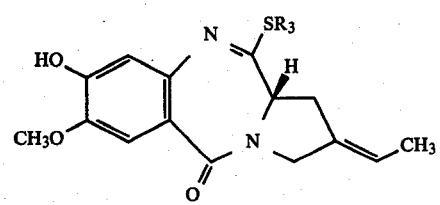

wherein $R_3$ is as defined above;

(5) selectively reducing the thioiminoether moiety of intermediate V or intermediate VI in an inert solvent to produce a thiocarbinolamine intermediate of the formula

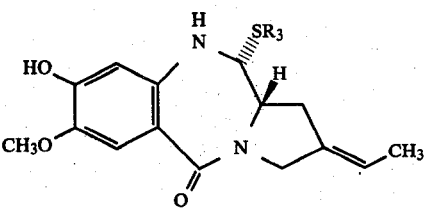

or

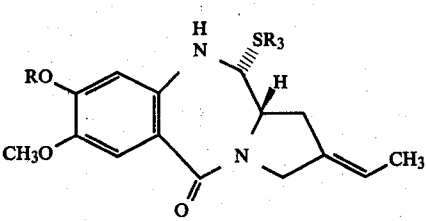

wherein R and $R_3$ are as defined above; and (6) reacting intermediate VII or VIII with a mercuric salt in methanol to form the carbinolamine product of the formula

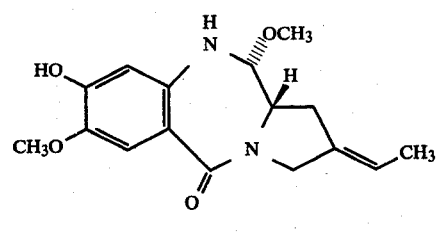

or

-continued

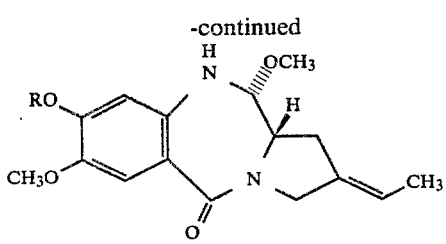
IX wherein R is as defined above; and, when the product obtained is compound IX, removing the hydroxyl protecting group R from intermediate IX so as to form the desired tomaymycin product I.

2. The process according to claim 1 which includes the additional step of converting tomaymycin to desmethanol tomaymycin of the formula

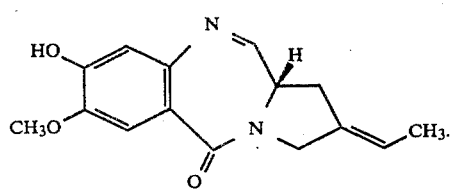
Ia

3. The process according to claim 1 or claim 2 wherein the reducing agent used in step (5) is aluminum amalgam.

4. The process according to claim 1 or claim 2 wherein
   (a) in step (1) the C-8 hydroxyl group is protected by a benzoyl group;
   (b) in step (2) the thiation reagent is 2,4-bis-(4-methoxyphenyl)-1,3-dithia-2,4-diphosphetane-2,4-disulfide;
   (c) in step (3) the alkylation is carried out using methyl iodide in tetrahydrofuran; and
   (d) in step (5) the reduction is carried out using aluminum amalgam in an aqueous ether solvent.

5. An intermediate of the formula

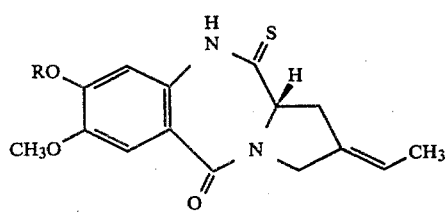

wherein R is a conventional phenolic hydroxyl protecting group.

6. The intermediate of claim 5 wherein R is benzoyl.

7. An intermediate of the formula

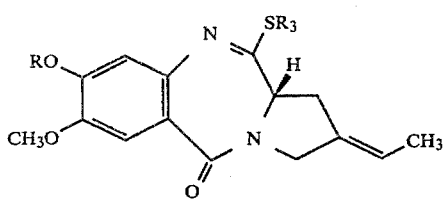

wherein $R_3$ is (lower)alkyl and R is a conventional phenolic hydroxyl protecting group.

8. The intermediate of claim 7 wherein $R_3$ is methyl and R is benzoyl.

9. An intermediate of the formula

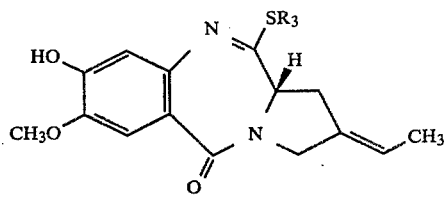

wherein $R_3$ is (lower)alkyl.

10. The intermediate of claim 9 wherein $R_3$ is methyl.

11. An intermediate of the formula

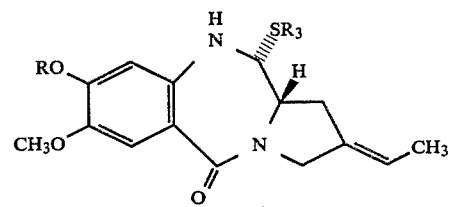

wherein $R_3$ is (lower)alkyl and R is a conventional phenolic hydroxyl protecting group.

12. The intermediate of claim 11 wherein $R_3$ is methyl and R is benzoyl.

13. An intermediate of the formula

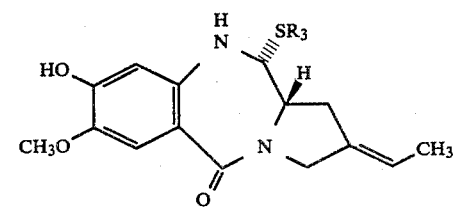

wherein $R_3$ is (lower)alkyl.

14. The intermediate of claim 13 wherein $R_3$ is methyl.

15. A process for the preparation of an intermediate of the formula

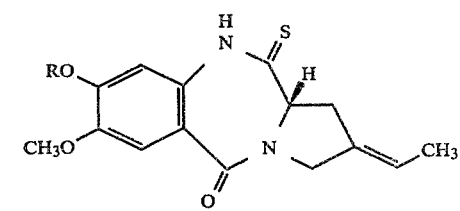

wherein R is a conventional phenolic hydroxyl protecting group, which process comprises reacting an amide intermediate of the formula

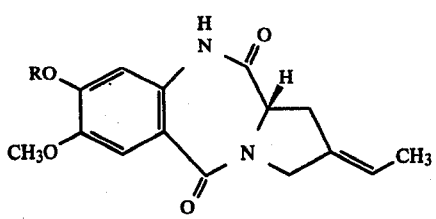

wherein R is as defined above with phosphorous pentasulfide or 2,4-bis(4-methoxyphenyl)-1,3-dithia-2,4-diphosphetane-2,4-disulfide in an inert organic solvent.

16. A process for the preparation of an intermediate of the formula

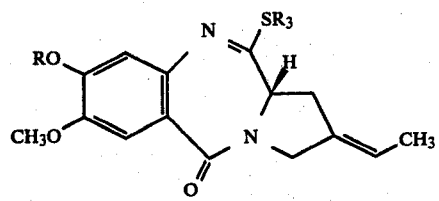

wherein $R_3$ is (lower)alkyl and R is a conventional phenolic hydroxyl protecting group, which process comprises reacting an intermediate of the formula

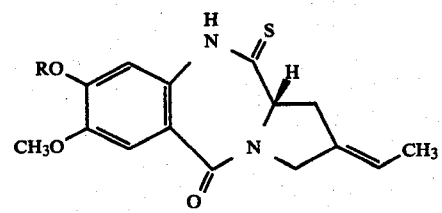

wherein R is as defined above with a (lower)alkyl halide or (lower) alkoxonium salt in an inert organic solvent and in the presence of base.

17. A process for the preparation of an intermediate of the formula

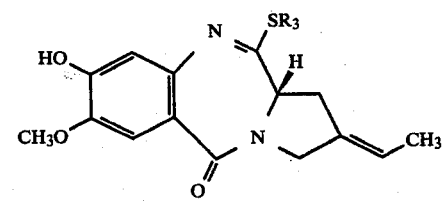

wherein R is (lower)alkyl, which process comprises removing the C-8 hydroxyl protecting group of an intermediate of the formula

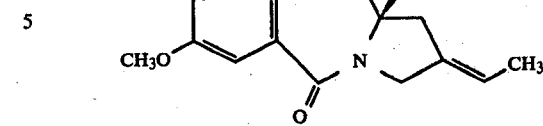

wherein R is a conventional phenolic hydroxyl protecting group.

18. A process for the preparation of an intermediate of the formula

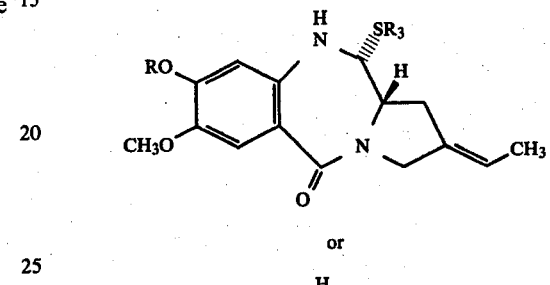

or

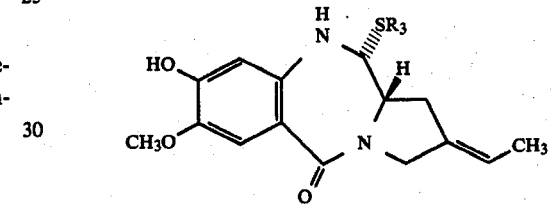

wherein R is a conventional phenolic hydroxyl protecting group, which process comprises selectively reducing in an inert organic solvent and in the presence of base the thioiminoether moiety of an intermediate of the formula

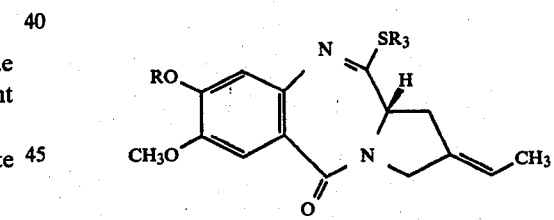

or

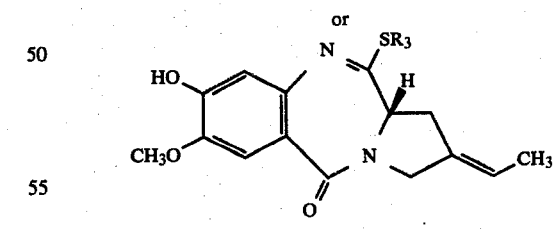

wherein $R_3$ is (lower)alkyl and R is a conventional phenolic hydroxyl protecting group.

* * * * *